(12) United States Patent
Mäkel et al.

(10) Patent No.: US 9,132,282 B2
(45) Date of Patent: Sep. 15, 2015

(54) BRACHYTHERAPY APPLICATOR DEVICE FOR INSERTION IN A BODY CAVITY

(75) Inventors: René Gerard Willem Mäkel, Arnhem (NL); Pieter Morssink, Bel Air, MD (US); Hendrik Steller, Rhenen (NL); Arie Luite Visscher, Driebergen (NL); Cor Van De Wardt, Kesteren (NL); Franciscus Antonius Maria Kuipers, Veenendaal (NL)

(73) Assignee: NUCLETRON OPERATIONS B.V., Veenendaal (NL)

( * ) Notice: Subject to any disclaimer, the term of this patent is extended or adjusted under 35 U.S.C. 154(b) by 232 days.

(21) Appl. No.: 13/807,552

(22) PCT Filed: Jun. 30, 2011

(86) PCT No.: PCT/NL2011/050474
§ 371 (c)(1),
(2), (4) Date: Apr. 8, 2013

(87) PCT Pub. No.: WO2012/002815
PCT Pub. Date: Jan. 5, 2012

(65) Prior Publication Data
US 2013/0204070 A1    Aug. 8, 2013

Related U.S. Application Data

(60) Provisional application No. 61/365,004, filed on Jul. 16, 2010.

(30) Foreign Application Priority Data

Jun. 30, 2010 (NL) ...................................... 2005005

(51) Int. Cl.
*A61N 5/10* (2006.01)

(52) U.S. Cl.
CPC ............ *A61N 5/1014* (2013.01); *A61N 5/1016* (2013.01)

(58) Field of Classification Search
CPC .................... A61N 2005/1012; A61N 5/1016; A61N 5/10; A61N 5/1014; A61N 5/1015; A61N 5/1018; A61N 5/1007
See application file for complete search history.

(56) References Cited

U.S. PATENT DOCUMENTS

| 4,350,151 A | 9/1982 | Scott |
| 2009/0234178 A1 | 9/2009 | Lebovic et al. |
| 2011/0224478 A1* | 9/2011 | Hannoun-Levi et al. ......... 600/6 |

FOREIGN PATENT DOCUMENTS

| DE | 44 13 490 C1 | 8/1995 |
| EP | 1 374 951 A1 | 1/2004 |
| WO | WO 2010/036103 A2 | 4/2010 |

OTHER PUBLICATIONS

International Search Report from the European Patent Office in PCT/EP2011/050474 mailed on Oct. 6, 2011 (2 pages).
(Continued)

*Primary Examiner* — Christine H Matthews
(74) *Attorney, Agent, or Firm* — Finnegan, Henderson, Farabow, Garrett & Dunner, LLP

(57) ABSTRACT

The invention relates to a brachytherapy applicator device for insertion in a body cavity. The applicator device comprises an applicator shaped for insertion in the body cavity; the applicator comprising connectable segments; at least one connectable part having a form following wall surface shaped to follow the body cavity, the wall surface having a multichannel groove structure, so as to guide a plurality of catheters along the grooves in the groove structure along the wall surface.

12 Claims, 13 Drawing Sheets

(56) References Cited

OTHER PUBLICATIONS

Figure 1:
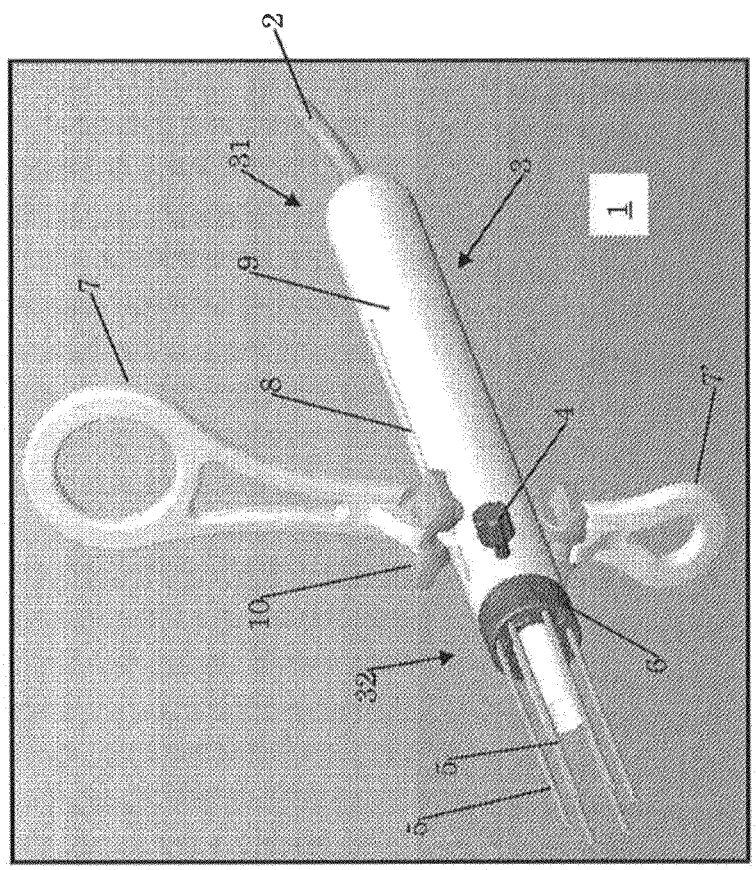

Notification of Transmittal of the International preliminary Report on Patentability and International Preliminary Report on Patentability from the European Patent Office in PCT/EP2011/050474 mailed on Nov. 6, 2012 (6 pages).

Official Action, issued in corresponding Russian Application No. 2013103770/14(005446), mailed Feb. 5, 2015 (8 pages including English language Translation).

* cited by examiner

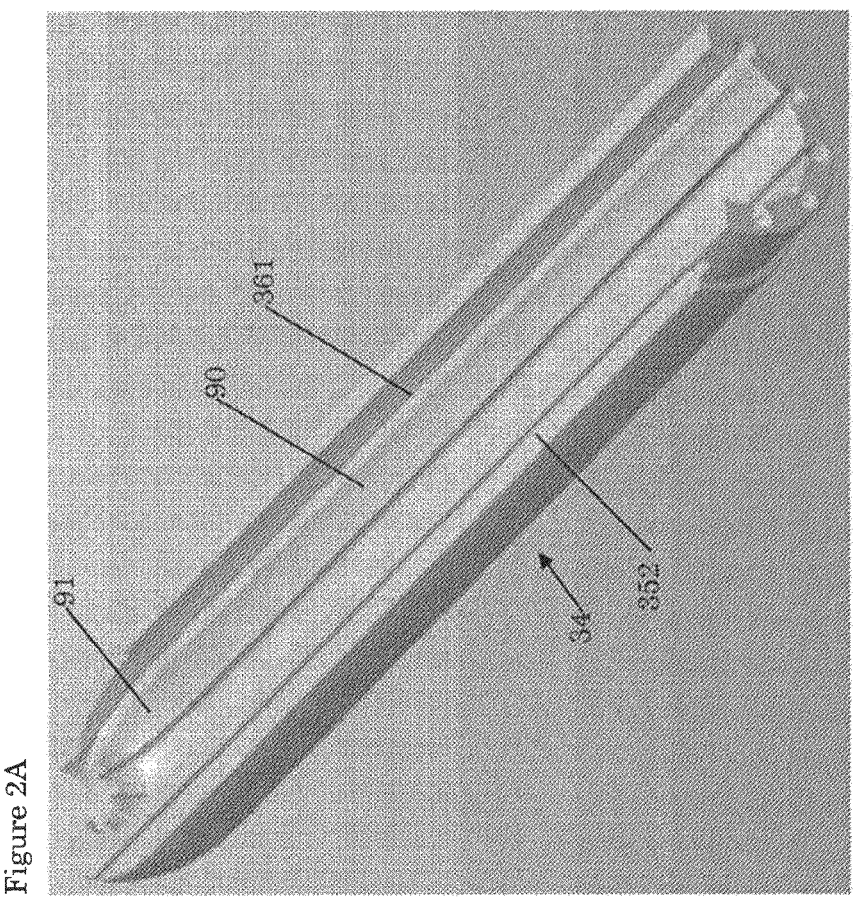

BRACHYTHERAPY APPLICATOR DEVICE FOR INSERTION IN A BODY CAVITY

This application is a U.S. national stage filing under 35 U.S.C. §371 of International Application No. PCT/EP2011/050474 filed on Jun. 30, 2011, which claims priority to Netherlands Application No. 2005005, filed on Jun. 30, 2010 and U.S. Provisional Application No. 61/365,004, filed on Jul. 16, 2010, all of which are incorporated herein by reference.

FIELD

The invention relates to a brachytherapy applicator device for insertion in a body cavity. In particular, the invention relates to a brachytherapy applicator device for irradiating tumours.

BACKGROUND

DE4413490 shows such an instrument of the cylindrical vaginal applicator type, where irradiation positions are realized by a central catheter which is introduced into the applicator. The applicator can be connected to a so-called remote afterloading machine which via tubes moves a radioactive source to an irradiation position in the central catheter. In this device some radiation shielding is provided by a central filler element which is inserted in the applicator and can be made from different materials to provide differential radiation shielding with a relatively limited control over the dose distribution.

Such an applicator may comprise multiple catheters provided along a wall part of the cylinder, which thereby generally follows the form of the body cavity wherein the applicator is inserted. The guidance of the catheters along the wall part enables the irradiation doses to be shaped and so optimised, whilst keeping the dose at the surface of the organ at or below the desired limit. The irradiation is done by bringing a radiation source provided at the end of a guide cable via a transfer tube and the catheter to a predetermined correct position and allowing it to deliver radiation there for a predetermined length of time to combat the tumour.

It is noted that conventional applicators are instruments assembled from complex parts and frequently comprise long guide through bores that are difficult to clean when sterilizing the instruments for repeated use.

It is an object of the invention to provide an instrument which can be assembled quickly and introduced easily into the body cavity and whose positioning is accurate and reliable. In addition, it is an object to provide an instrument that is easily dis-assembled and so can easily be cleaned and sterilized.

SUMMARY

According to an aspect, a brachytherapy applicator device is provided for insertion in a body cavity, comprising an applicator shaped for insertion in the body cavity; the applicator comprising connectable parts;
  at least one connectable part having a form following wall surface shaped to follow the body cavity, the wall surface having a multichannel groove structure, so as to guide a plurality of catheters along the grooves in the groove structure along the wall surface.

The groove structure provides efficient and reliable guiding of irradiation catheters at a predetermined distance from the cavity wall while at the same time being easy to clean. In addition, the segments allow for quick assembly and disassembly of the applicator, so that the constituting segments are exposed for cleaning.

EXEMPLARY EMBODIMENTS

Figure 2:
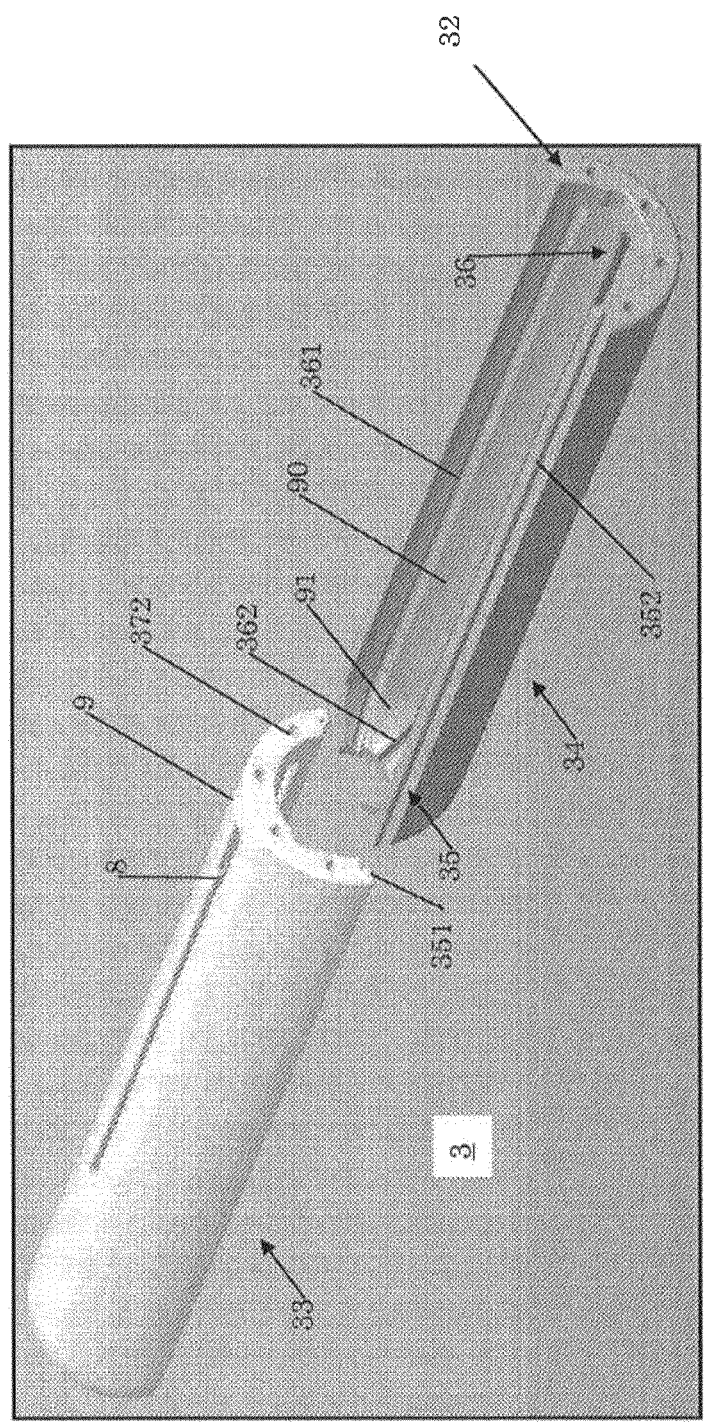
Figure 2B:
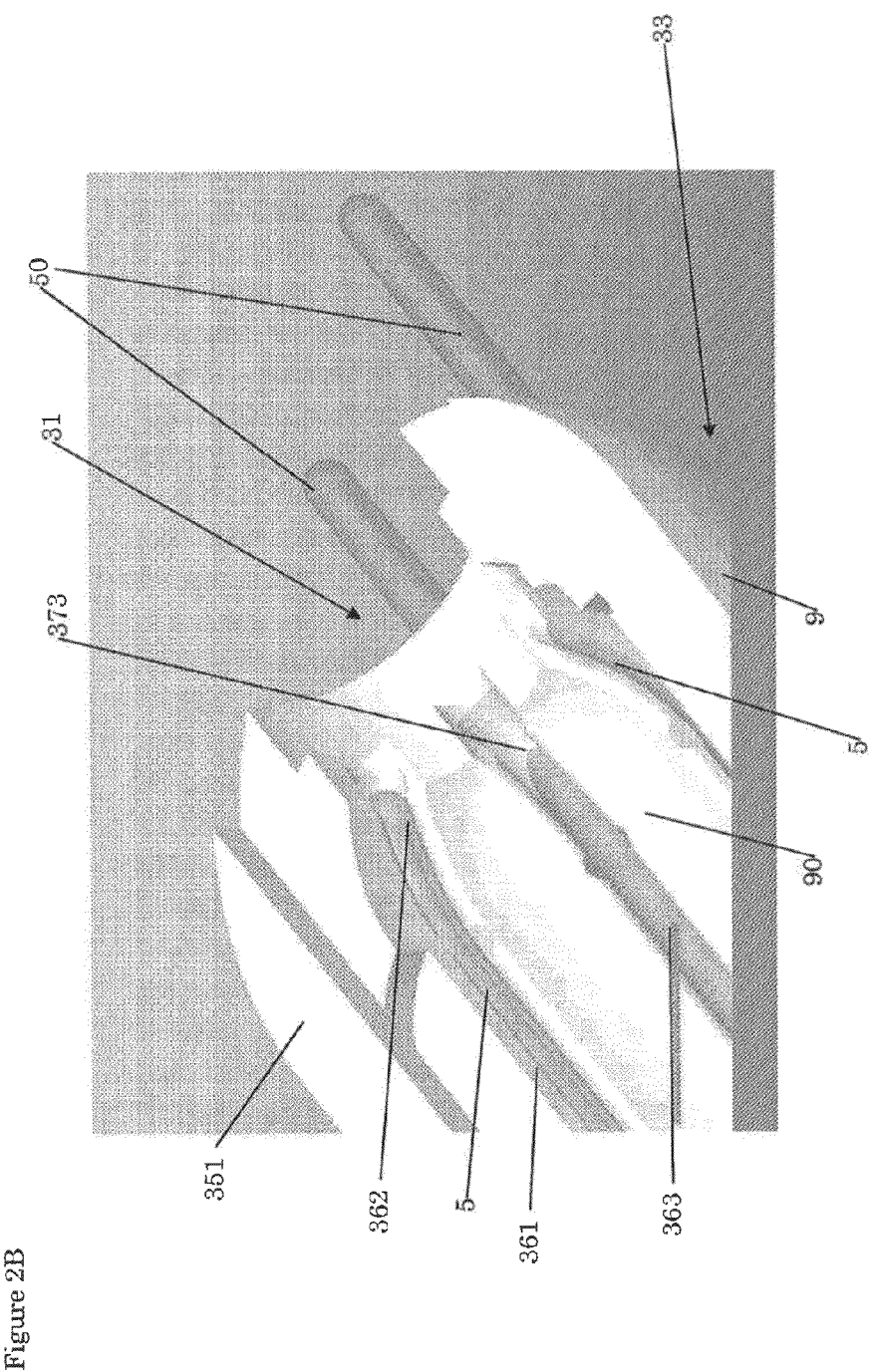
Figure 2C:
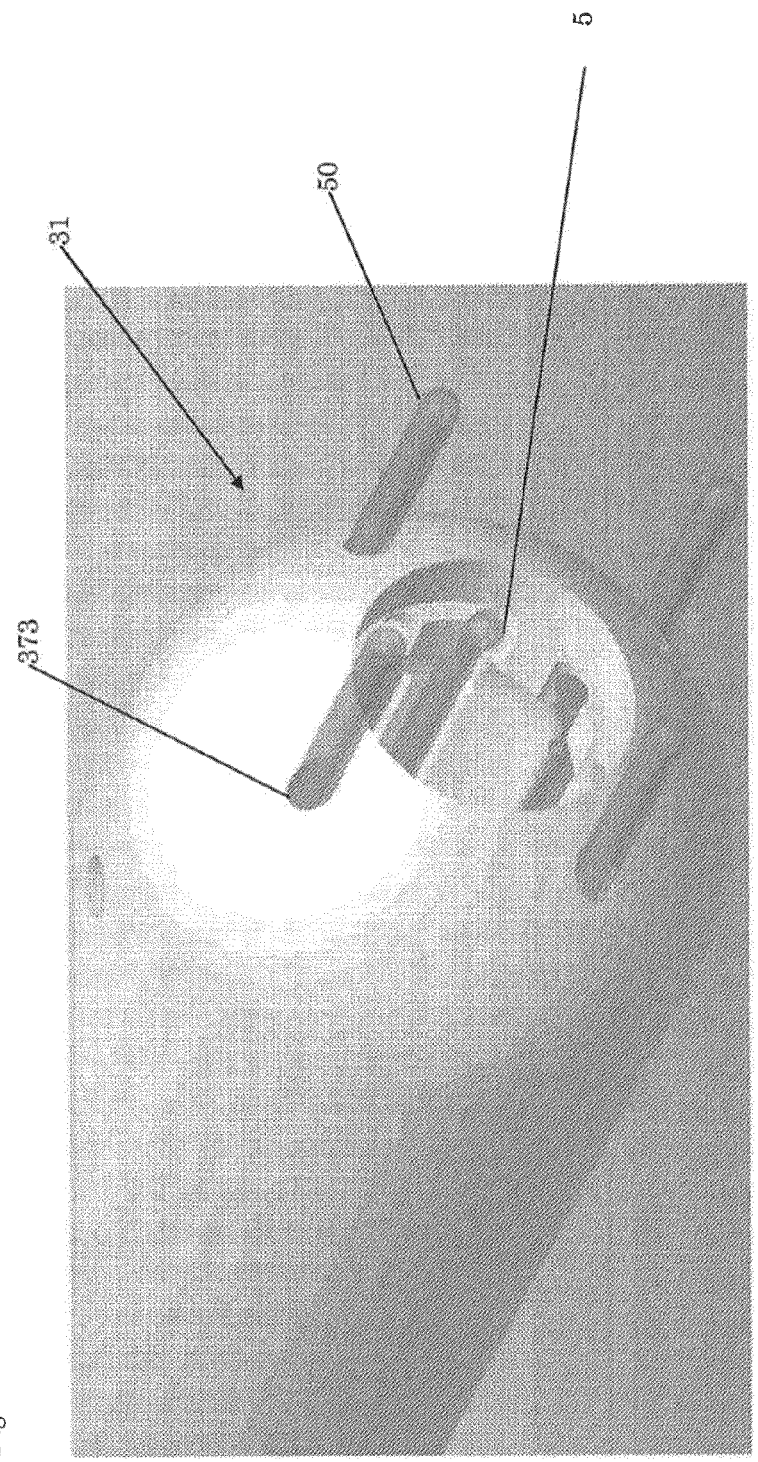
Figure 3:
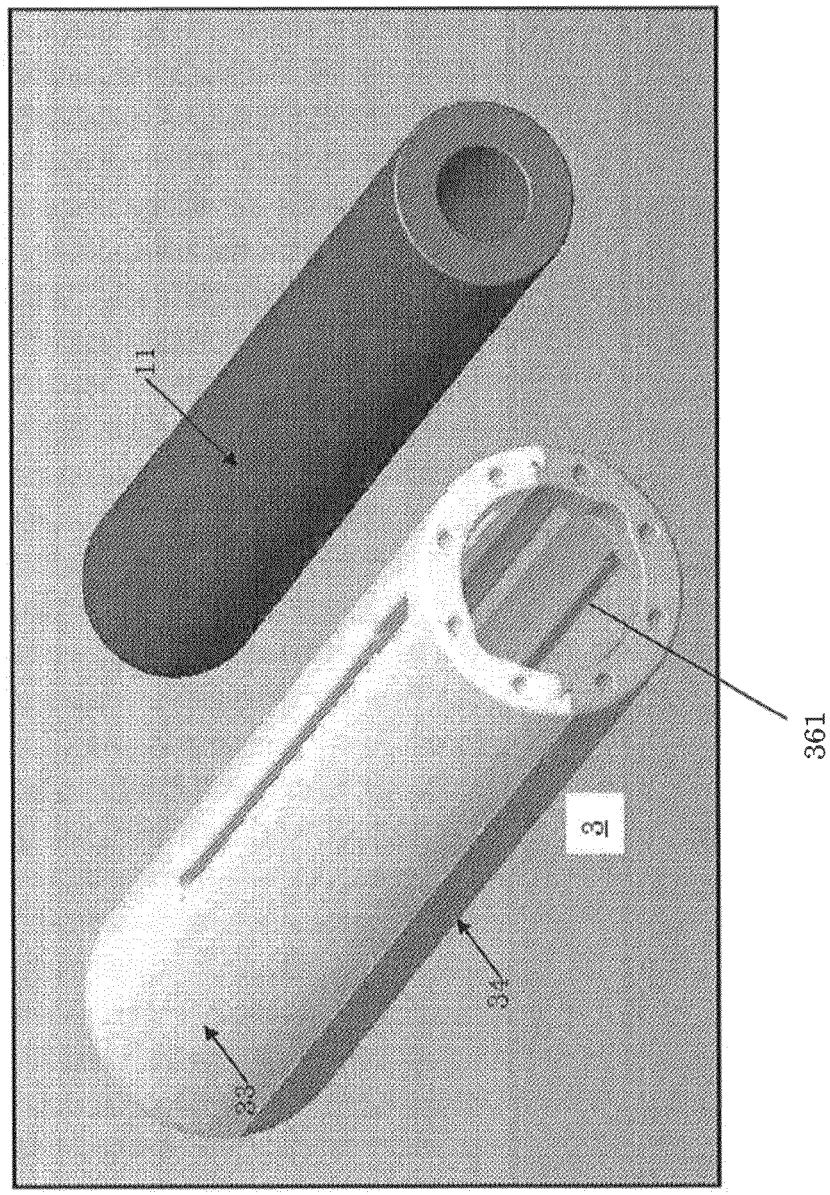
Figure 4:
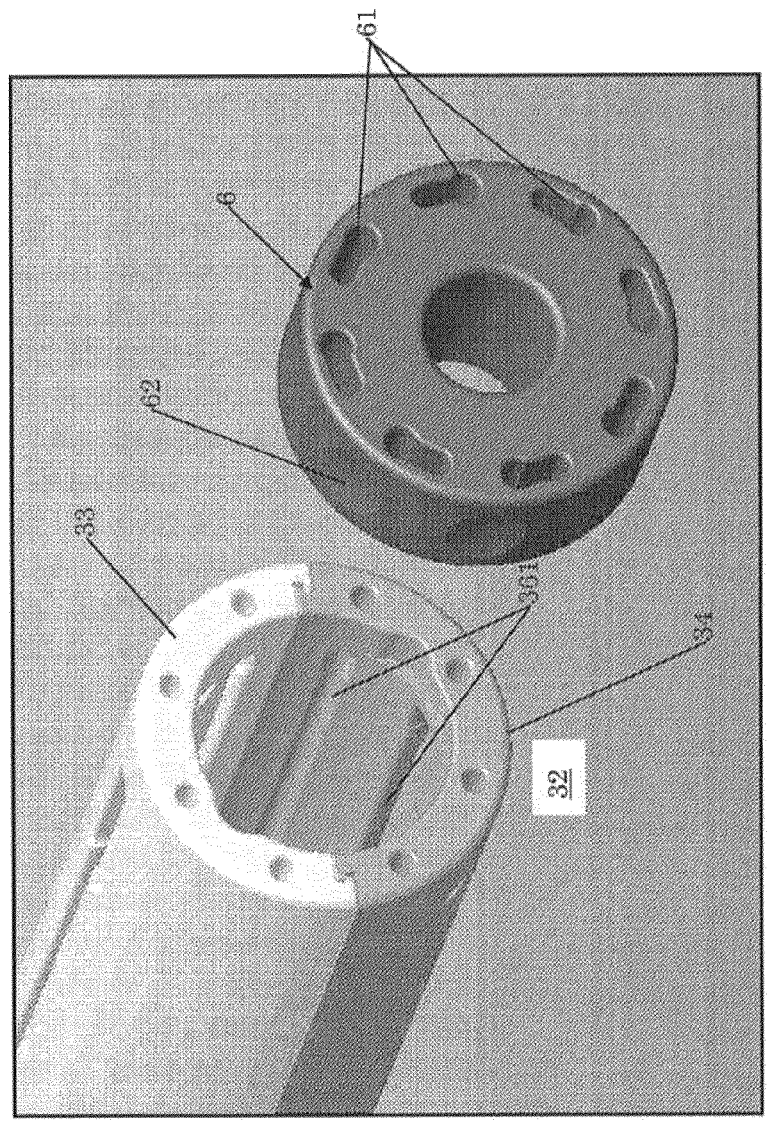
Figure 5:
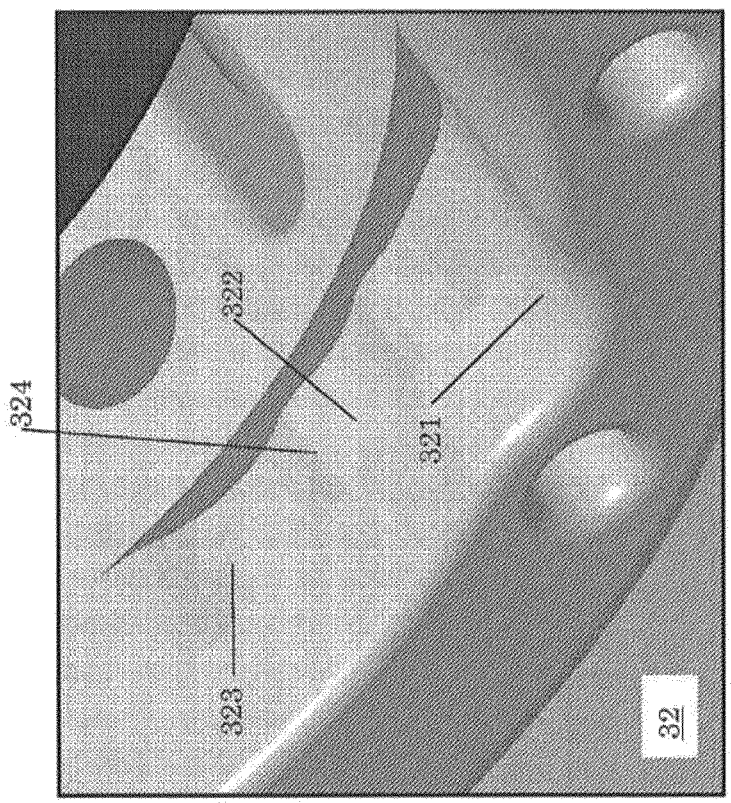
Figure 6:
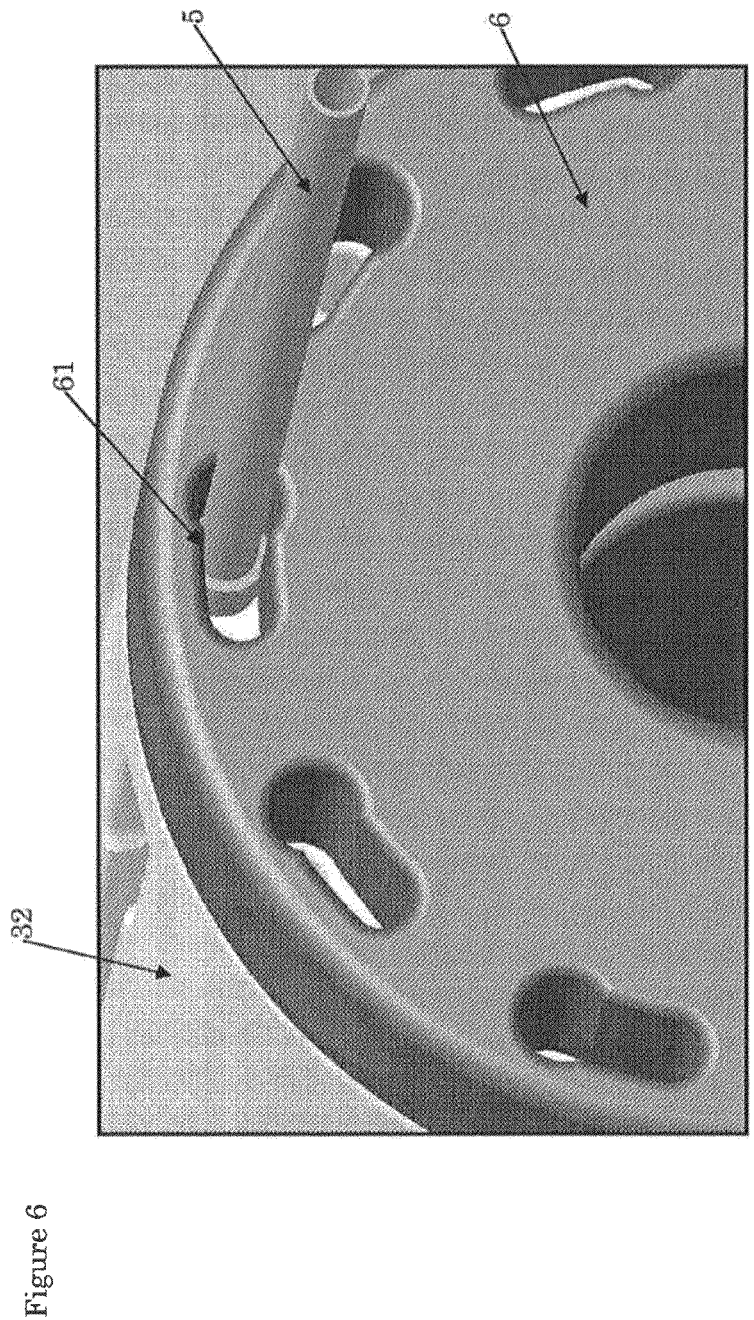
Figure 7:
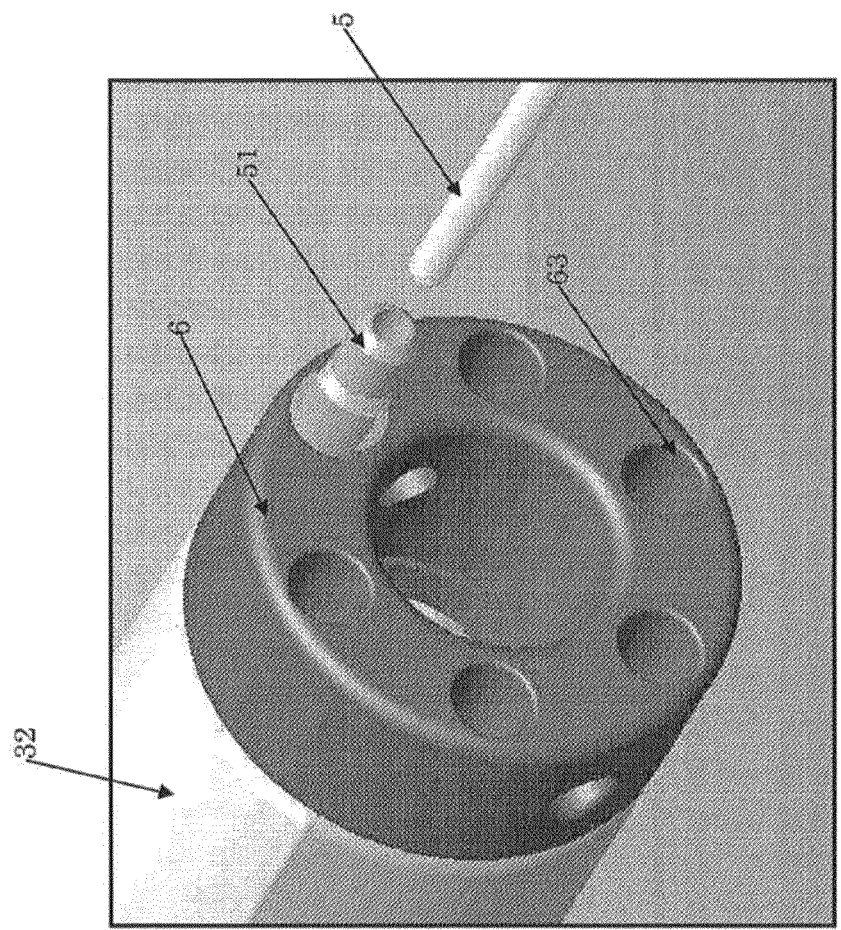
Figure 8:
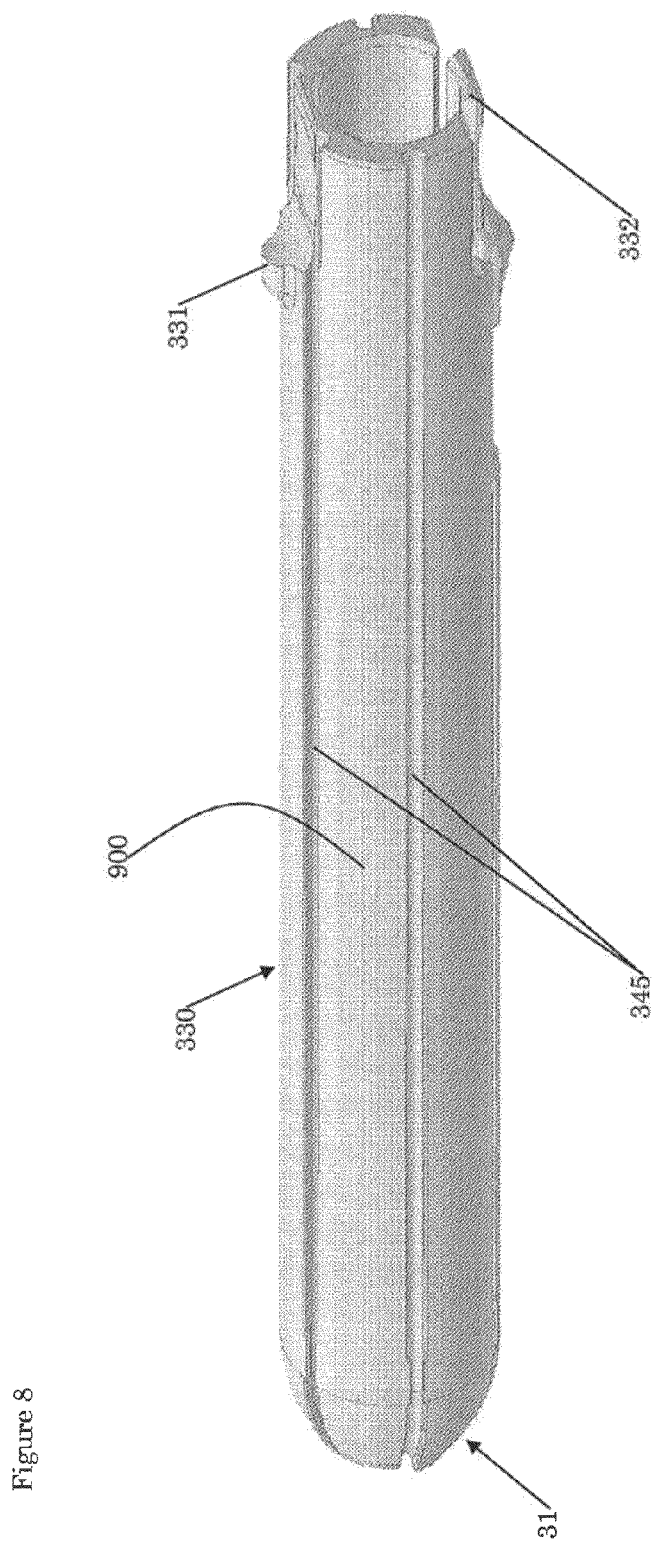
Figure 8B:
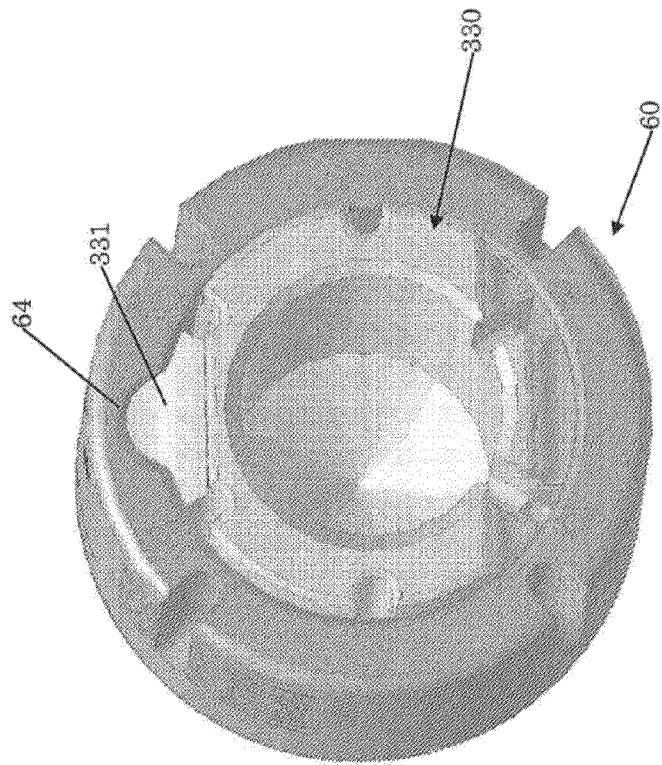
Figure 8A:
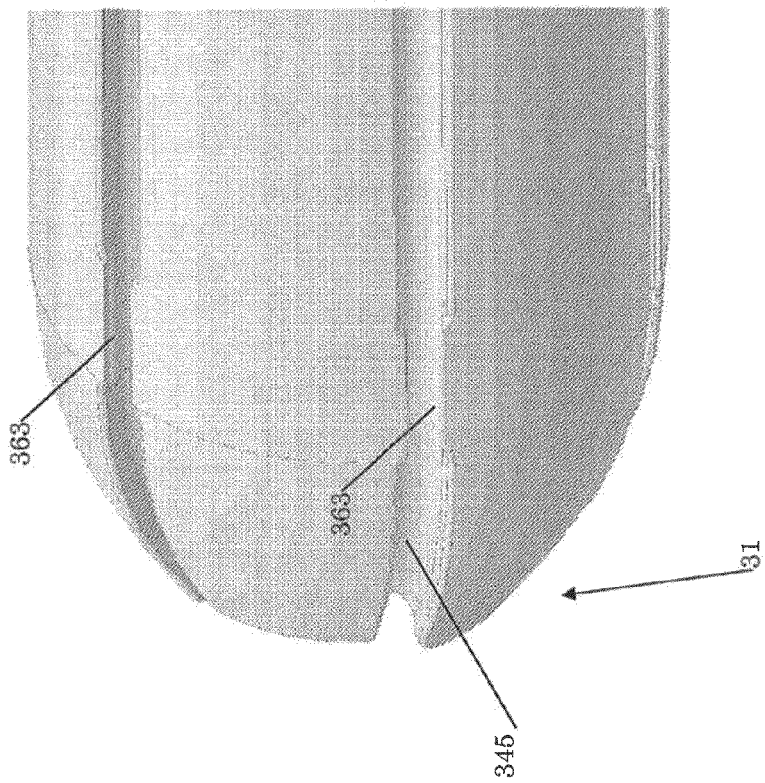
Figure 9:
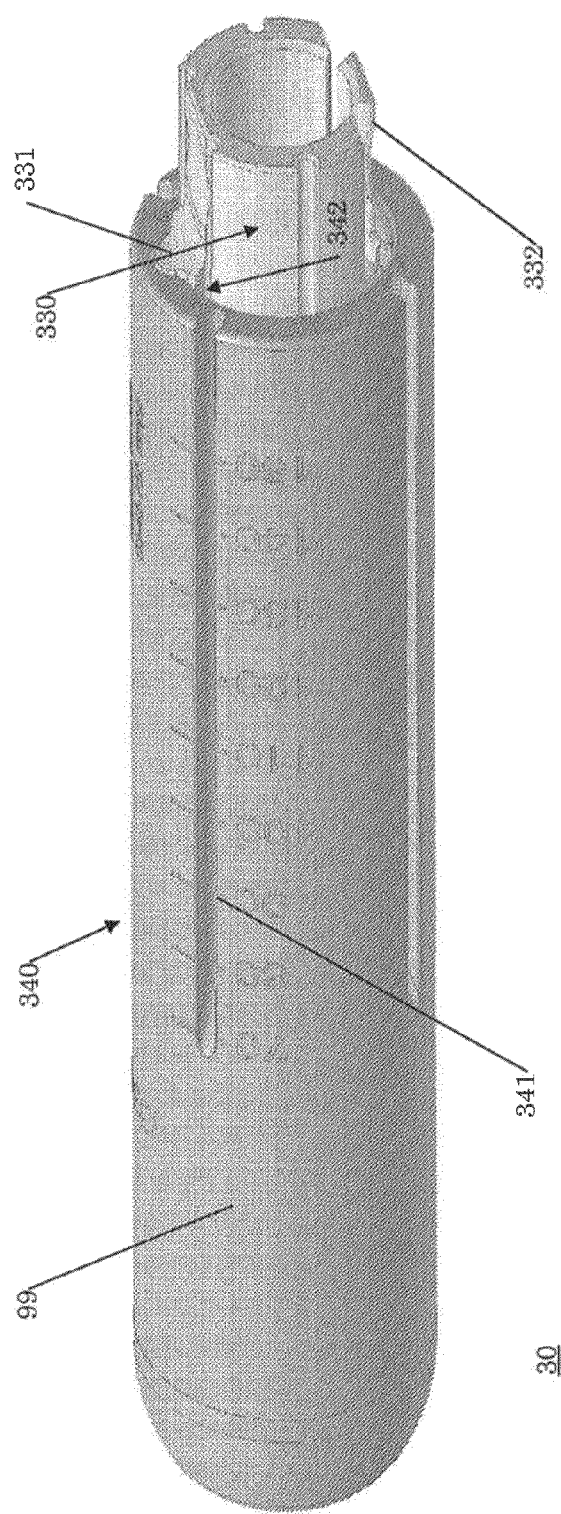

The invention will be elucidated in more detail in and by a description of the drawings, in which:
  FIG. 1 shows a complete assembly of an applicator device;
  FIG. 2 shows a perspective view of a two-piece applicator of the applicator device in disassembled condition;
  FIG. 2A shows a sectional view of an alternative segment of the applicator;
  FIG. 2B shows a sectional view of a further alternative segment of the applicator;
  FIG. 2C shows a front perspective view of the alternative segment;
  FIG. 3 shows a perspective view of the applicator of FIG. 2 in assembled condition;
  FIG. 4 shows a view of proximal part of the applicator of FIG. 3 in disassembled condition;
  FIG. 5 shows a detailed view of the proximal part of FIG. 2;
  FIG. 6 shows a schematic perspective view of the keyhole structure in the proximal part in particular;
  FIG. 7 shows an alternative cap structure;
  FIG. 8 shows a connectable part of an alternative applicator device
  FIGS. 8a and 8b shows a detailed view of the distal and proximal parts respectively; and
  FIG. 9 shows the applicator device having a sleeve structure slided on the connectable part.

In the drawings, the same or corresponding parts are designated by the same reference numerals.

FIG. 1 shows a complete assembly of an applicator device 1. In assembled condition, a brachytherapy applicator device 1 is provided for insertion, in a body cavity. The assemblies and components described herein would be suitable for administration of all types of brachytherapy treatment. This applicator can be used for treatment of gynaecological tumours of the vagina and cervix and can also be used for the treatment of colo-rectal tumours or those affecting the endometrium. During brachytherapy treatment energy emitting (radioactive) sources are inserted near or into the tumourous tissue of the human or animal body to be treated. For this purpose, an active energy emitting source is used to administer what is generally known as High Dose Rate (HDR) treatment. In HDR treatment the radiation source is guided into the tissue or body cavity for one or more periods by means of a needle or a catheter and is always contained within a closed capsule so it never comes into direct contact with the tissue. Brachytherapy can also be performed with PDR (pulse dose rate) or LDR (low dose rate) treatments. In addition, as long as the applicator is shaped in a corresponding effective form the applicator device may be used for any intracavitary or interstitial treatment.

In this embodiment the version of the applicator, which comprises a plurality of connectable parts, could be used for treatment of gynecological tumours of the vagina and cervix will be described. In more detail, the embodiment shows further an optional central intrauterine tube 2 that can be fixed relative to the applicator 3 and which is guided through a central opening in the dome-shaped distal end 31 of the applicator 3. The intra-uterine tube 2 is provided with a positioning means 4 for fixation relative to the applicator. This means comprises in the exemplary embodiment a fixation screw. In this embodiment, the intra-uterine tube is of fixed length, but an adjustable length tube could be used. In a further alternative, different angles can be used to provide suit different patient anatomies. The intra-uterine tube 2 accordingly serves for insertion into the cervix and can be used for intrauterine irradiation. Exemplary for an applicator form shaped for insertion into the body cavity, is a multi-channel cylindrical type of the present embodiment, which has a form following wall surface shaped to follow the body cavity. In this embodiment, the applicator comprises a plurality of guiding grooves in the wall for guiding catheters 5 along their respective longitudinal axes and restrain the catheters 5 against motion in a direction away from their longitudinal axes. In addition the device 1 further comprises a catheter locking structure, in this example in the form of a cap 6 on the proximal part 32 further detailed in FIG. 4 and FIG. 6 that locks the catheters 5 against axial movement relative to the applicator 3. After placement, during the irradiation, a high dose can be delivered to the base of the uterus without the surrounding organs such as large intestine and bladder needing to be irradiated unduly heavily. Preventing this excessive irradiation is of major importance since otherwise serious complications may be expected. A connectable handle 7 known as a perineal bar is slidingly engageable in a corresponding slot 8. The slot 8 is arranged along an outer surface 9 of the applicator 3. For fixation, a knob or lever 10 is provided which fixes the perineal bar 7 relative to the groove 8. The knob 10 has a cam structure which fixes the bar 7 when rotated. The perineal bar can be selectively provided in various sizes 7, 7' and fixed on one or either side of the applicator 3.

FIG. 2 shows the applicator 3 in more detail. The applicator is formed by two connectable parts 33 and 34 having connectors 35 for ready connection. The connectors 35 are provided by mating shoulder pieces or wedges 351, 352, each arranged on opposite end sides of the connectable segments 33, 34 each forming a partly tubular shaped segment. Alternatively a fastener 35 can be provided by, for example, in the form of a locking groove and a locking knob to be locked in sliding engagement in a corresponding locking slot. An alternative locking structure may for example be provided by a dovetail type joint providing interlocking with conventional locking shapes.

The wall surface comprising the groove structure 36 is advantageously distanced from the body surface, but this is not essential; it may be formed as an outer surface that is in direct contact with the body cavity or by a surface distanced from the outer surface such as in the present example. In this example, inner wall surface 90 has a multichannel groove structure 36 that is provided to guide the catheters 5 along grooves 361 in the groove structure 36 along the wall surface. Alternatively, the groove structure 36 may be provided on the outer surface 9, in addition to the locking slot 8 for the perineal bar 7 (see FIG. 1).

The grooves 361 may be formed as open trench structures that can be the continuations of through holes 372 of a relatively short depth that may be provided on the segment edges, in particular, the proximal part 32 thereof. Alternatively, the grooves may be continued without through holes 372, as shown in FIG. 2A. While FIG. 2 shows an applicator comprised of two segments 33, 34, the tubular applicator could be formed of more segments which may be connected together. Each segment may be provided with one or more grooves 361 on inner wall 90.

In a further alternative, shown in FIG. 2B, in a sectional view of a segment 33, in particular, its dome shaped distal part 31, through hole guides 373 can be combined with open grooves 363 arranged on inner wall 90 to provide a (nearly) straight catheter guide for a catheter 50 extending from a groove 363 in axial direction out of the dome shape 31 via through holes 373. The concept here is that a further groove structure may comprise grooves 363 extending via respective through holes 373 out of the dome shape 31 so that a catheter 50 following the further groove structure continues straight on out of the applicator and is capable of penetrating the surrounding tissue.

The connecting functionality of the structure is similar in as the FIGS. 2 and 2a embodiment with a wedge 351 arranged for mating with a corresponding wedge of another segment (not shown).

An important aspect of the grooves, in addition to their favourable cleaning properties, is that they facilitate in guiding the catheter along curved surface 91, particularly for instance, in the dome shaped distal end 31 where the segment 34 is shaped to have a rounded inner wall part 91 comprising a groove 362 curved in the axial direction along a center axis of the applicator. FIG. 2C shows a schematic front view of dome shape 31

Accordingly, in the embodiment of FIGS. 2B and 2C, a catheter 5 may follow the groove structure 36 radially around the dome shape 31 via curved groove 362; or a catheter 50 may follow a straight guiding path via a through hole 373. The catheters 5, 50 may be of the same kind, or may be formed purposely, for example, a straight catheter 50 may be more rigid than a curved catheter 5.

Advantageously, the grooves with a grooved path 361, grooves with a straight path 363 may at least partly lie on a same (semi) circular circumference of the tubular segment 33, 34, in particular, on its inner wall 90. Conversely, grooves may be arranged on the outer wall as illustrated in the example below, or in a mixed form with both walls, for example, straight grooves arranged on the outer wall and dome shaped grooves on the inner wall 90. In addition, for example, through hole guides can also be arranged near a wall part 9 opposite the groove structure on the inner wall 90, so that radiation can be provided via further catheters arranged in through hole guides axially following the outer wall 9 (not shown).

The curved grooves are important in improving the dose distribution at the distal end 31 of the applicator. With this curved guidance of the catheters, the cervix area can be reached better so helping to improve dose distribution with the aim of optimizing the radiation treatment.

Whilst the drawings in FIG. 2 show two semi-cylindrical segments which can be connected together this can be formed by more than two components, for example, three or four semi circular segments. Each of those separate segments could therefore have a different configuration of channels for the catheter. Thus, a segment could only comprise "straight-through" channels such as grooves 363 and another could be or include the curved grooves 361. An advantage of the multiple segments is that different types of segment could be selected and the applicator could almost be "customised" to provide a specific dose profile according to the need of the patient. Accordingly, multiple segments can each be provided with a designated groove structure.

FIG. 3 shows the segments 33 and 34 in assembled condition. A filler tube 11 may be provided. Advantageously the filler piece 11 may comprise a plurality of interlocking segments (not shown) made from different materials having different radiation shielding properties, which can differentially reduce the dose of the radiation emitted from the catheters and passing through the applicator. This is advantageous for calculation purposes. Optionally the filler tube could be formed from a plurality of interlocking segments arranged in such a manner to tune the radiation profile. The filler tube 11 may form a close fit inside the cylindrical segments 33 and 34 for ensuring the catheters remain inside the grooves 361. Alternatively, as shown in the present embodiment, the groove structure comprises a groove 361 that locks the catheter along a more than semicircular circumference.

The present embodiment thus forms a brachytherapy applicator device for insertion in a body cavity, comprising an applicator 3 shaped for insertion in the body cavity; the applicator 3 comprising a plurality of connectable parts 33, 34 at least one of the connectable parts 33, 34 having a first wall surface 9 shaped to follow the body cavity, a second wall surface 90 having a plurality of catheter guide grooves 36 therein capable of guiding a catheter 5 along a groove 361, a third wall surface 11 cooperating with the second wall surface 90 to maintain the catheter in the groove when the applicator is assembled.

FIG. 4 shows in more detail the applicator's proximal end 32 and cap 6. The cap 6 may be optionally provided and has advantageous locking features. Not shown are connectors of cap 6 connectable to the cylinders' proximal end 32. For locking the catheters, the cap 6 comprises a catheter locking structure 61 aligned with the groove structure 361. In the example, the catheter locking structure 61 is formed by keyholes provided in the cap 6 and aligned with a corresponding groove 361 in the cylinder segments 33, 34. The cap 6 can be rotated to lock the catheter 5 in the keyhole 61. Accordingly, cap 6 is to guide catheters 5 through keyholes 61 and has a central opening for passing of the intrauterine tube 2. Depressions 62 are provided for providing grip.

As an example of a cap connector structure, FIG. 5 shows a detail of a proximal end 32 of the applicator, in particular, L-shaped recess 321. The cap connectors are formed by resilient locking knobs (not shown). The recess 321 accordingly receives a knob provided on cap 6 (not shown) and can be clicked in the recess 321 from an unlock to a lock position (322, 323) via a local thickening 324 provided in the recess 321.

FIG. 6 shows the cap 6 in mounted position, wherein it can be seen that a catheter 5 is provided that is guided through keyhole 61 and is shown in locking position.

FIG. 7 shows an alternative locking mechanism, wherein the locking structure is formed by catheter locking insert 51 to be inserted in a corresponding recess 63 arranged in the cap. By way of example, such inserts 51 can fixate the catheter 5 by twisting it in a corresponding threaded part or by a bayonet click conventionally known.

FIG. 8 shows a connectable part comprising a core piece 330 of an alternative applicator device. In this embodiments, the core piece 330 is not segmented but tubular shaped and forms a core piece of the applicator device 30 illustrated in more detail in the following figures. The core piece 330 has an elongated rounded form shaped for insertion into a cylinder 340 (see FIG. 9) which has a substantially smooth inner wall surface. The cylinder 340 forms an outer sleeve of an applicator device which can be inserted into a body cavity such as the vagina or rectum. The core piece 330 has a multichannel groove structure 36 on the outer surface of the wall 900, to guide a plurality of catheters along the grooves 345 in the groove structure along the outer wall surface 900.

FIG. 8a shows a detailed view of the distal part of the core piece 330, where it can be shown that the applicator has a dome-shaped distal end portion 31, the groove 345 extending into the distal dome shaped end portion and curved towards a central region of the dome 31. In addition, tongue structures 363 are used to enclose more than a semicircular circumference in order to retain the catheter (not shown) in the groove.

In use, brachytherapy catheters can be easily inserted in and removed from the groove structure 345, prior to assembly or disassembly.

FIG. 8b shows a proximal view of the core piece 330. A cap 60 is connectable to a proximal end of the applicator core piece 330 via a slot 64 that engages a knob 331 on the core piece 330. The cap may include a catheter locking structure similar in operation as the previous embodiment which can lock or unlock by rotating the cap 60.

FIG. 9 shows the applicator device having a sleeve 340 connected over the core piece 330 in assembled form. The sleeve 340 is located in the correct orientation over the core piece 330 by knob 331 engaging a cooperating slot on the outer sleeve 340 and maintained in position by a latching tooth which engages in a cooperating latching recess in the outer sleeve 340. The pressbar 332 arranged on the core piece 330 can be pressed inwards towards the centre of the core piece to release the parts. The sleeve 340 discloses marks 341 for accurately locating a sliding a bar similar to the perineal bar 7 disclosed in FIG. 1. Alternatively, the marks can be used as an indication of the depth of insertion of the applicator into the body cavity.

The present embodiment thus forms a brachytherapy applicator device for insertion in a body cavity, comprising an applicator 30 shaped for insertion in the body cavity; the applicator 30 comprising a plurality of connectable parts 330, 340 at least one of the connectable parts 330, 340 having a first wall surface 99 shaped to follow the body cavity, a second wall surface 900 having a plurality of catheter guide grooves 345 therein capable of guiding a catheter 5 along a groove 361, a third wall surface 342 cooperating with the second wall surface 900 to maintain the catheter in the groove 345 when the applicator is assembled.

The insert piece and catheters are preferably made from a plastics material. Preferably, the catheters are sufficiently flexible to allow bending in the groove structure. Although the invention has been elucidated with reference to the examples shown in the drawings, the invention is not limited thereto but may also comprise variations or modifications without deviating from the spirit of the invention. The groove structure may be formed in an applicator outer surface directly in contact with the body cavity. In addition, where the text refers to a tubular shape, these shapes are understood to encompass any suitable round or elliptical forms and which may be of cylindrical, sleeve form and even slightly curved along the length axis. The scope of the invention is determined by the following claims.

The invention claimed is:

1. A brachytherapy applicator device for insertion in a body cavity, comprising:
    an applicator shaped for insertion in the body cavity, the applicator including connectable parts, which include an inner part and an outer sleeve part,
    wherein at least the outer sleeve part has a form following wall surface shaped to follow the body cavity, and wherein either an inner wall surface of the sleeve part or an outer wall surface of the inner part has a multichannel open groove structure distanced from the form following wall surface, so as to guide a plurality of catheters along grooves in the groove structure along the inner wall surface of the sleeve part or the outer all surface of the inner part,
    wherein the device further includes a cap having cap connectors connectable to a proximal end of the applicator, the cap having a catheter locking structure aligned with the groove structure, wherein the catheter locking structure is formed by a keyhole provided in the cap and aligned with a corresponding groove of the open groove structure, and wherein the cap can be rotated to lock at least one of the plurality of catheters in the keyhole.

2. Brachytherapy applicator device according to claim 1, wherein at least one of the connectable parts has a tubular shape along at least part of its respective length.

3. Brachytherapy applicator device according to claim 1, wherein at least one of the connectable parts includes a partly tubular-shaped segment.

4. Brachytherapy applicator device according to claim 1, wherein the applicator has a dome-shaped distal end portion, with at least one groove of the open groove structure extending into the dome-shaped distal end portion and curved towards a central region of the dome-shaped distal end portion.

5. Brachytherapy applicator device according to claim 1, wherein at least one groove of the open groove structure is constructed, along at least a part of the at least one groove's respective length, to enclose more than a semicircular circumference in order to retain at least one of the plurality of catheters in the groove.

6. Brachytherapy applicator device according to claim 1, wherein the inner part provides a means for assisting in retaining at least one of the plurality of catheters in the groove structure.

7. Brachytherapy applicator device according to claim 6, wherein the inner part comprises a plurality of interlocking segments made from different materials having different radiation shielding properties.

8. Brachytherapy applicator device according to claim 1, wherein the connectable parts are provided with mating surfaces arranged on opposite end sides of the parts.

9. Brachytherapy applicator device according to claim 1, wherein the applicator is tubular and the connectable parts are formed by partly tubular segments defining a dome-shaped distal end, wherein any catheters inserted into the applicator device will follow the groove structure radially around the dome-shaped distal end.

10. Brachytherapy applicator device according to claim 9, further comprising a central intrauterine tube that can be fixed relative to the applicator and which extends from a central opening in the dome-shaped distal end.

11. Brachytherapy applicator device according to claim 1, wherein the cap connectors are formed by resilient locking knobs.

12. Brachytherapy applicator device according to claim 1, further comprising a connectable handle slidingly engageable in a corresponding slot of at least one of the connectable parts.

* * * * *